(12) United States Patent
Friedman

(10) Patent No.: US 8,187,615 B2
(45) Date of Patent: May 29, 2012

(54) NON-AQUEOUS COMPOSITIONS FOR ORAL DELIVERY OF INSOLUBLE BIOACTIVE AGENTS

(76) Inventor: Doron Friedman, Karme-Yosef (IL)

( * ) Notice: Subject to any disclaimer, the term of this patent is extended or adjusted under 35 U.S.C. 154(b) by 1443 days.

(21) Appl. No.: 10/585,298

(22) PCT Filed: Dec. 19, 2004

(86) PCT No.: PCT/IL2004/001144
§ 371 (c)(1),
(2), (4) Date: Jul. 6, 2006

(87) PCT Pub. No.: WO2005/065652
PCT Pub. Date: Jul. 21, 2005

(65) Prior Publication Data
US 2007/0190080 A1     Aug. 16, 2007

(30) Foreign Application Priority Data
Jan. 6, 2004   (ID) .......................... 159729

(51) Int. Cl.
*A61K 9/00* (2006.01)
*A61K 38/00* (2006.01)
*A61K 48/00* (2006.01)
*A61K 31/70* (2006.01)
(52) U.S. Cl. ........... 424/400; 514/1.1; 514/44 R; 514/23
(58) Field of Classification Search ........................ None
See application file for complete search history.

(56) References Cited

U.S. PATENT DOCUMENTS

| | | | |
|---|---|---|---|
| 5,342,625 A * | 8/1994 | Hauer et al. .................. | 424/455 |
| 5,965,160 A | 10/1999 | Benita et al. | |
| 5,993,858 A | 11/1999 | Crison et al. | |
| 6,054,136 A | 4/2000 | Farah et al. | |
| 6,140,375 A | 10/2000 | Nagahama et al. | |
| 2003/0149061 A1 * | 8/2003 | Nishihara et al. .......... | 514/266.3 |

FOREIGN PATENT DOCUMENTS

| | | | |
|---|---|---|---|
| GB | 2222770 A | | 3/1990 |
| JP | 2002-121929 | | 5/1990 |
| WO | 96/13273 | * | 5/1996 |
| WO | 200056346 A1 | | 9/2000 |

OTHER PUBLICATIONS

Pouton, "Formulation of Self-Emulsifying Drug Delivery Systems" Advanced Drug Delivery Reviews, 25:47-58 (1997).
Lawrence and Rees, "Microemulsion-based media as novel drug delivery systems" Advanced Drug Delivery Reviews, 45:89-121 (2000).
He et al., "Microemulsions as drug delivery systems to improve the solubility and the bioavailability of poorly water-soluble drugs" Expert Opin. Drug Deliv. 7:445-460 (2010).
Prajpati et al. "Effect of differences in Fatty Acid Chain Lengths of Medium-Chain Lipids on Lipid/Surfactant/Water Phase Diagrams and Drug Solubility" J. Excipients and Food Chem, 2:73-88 (2011).

* cited by examiner

*Primary Examiner* — Robert A Wax
*Assistant Examiner* — Jessica Worsham
(74) *Attorney, Agent, or Firm* — Browdy and Neimark, PLLC

(57) ABSTRACT

The present invention provides a composition of low water solubility drug, dissolved or dispersed in a non crystalline or low crystalline form in an emulsion type composition of internal oily-solvent and external non-hydrous and water soluble solvent, whereas 1) emulsifying stabilizer comprises low fraction of the composition, and 2) emulsions of mean droplets size below one micron is obtained upon dilution with physiological fluids, and 3) facilitated dispersion of biologically active agents in body fluids is obtained, and more particularly to facilitating biological availability or improving clinical performance.

20 Claims, No Drawings

NON-AQUEOUS COMPOSITIONS FOR ORAL DELIVERY OF INSOLUBLE BIOACTIVE AGENTS

The present invention provides a composition of low water solubility drug, dissolved or dispersed in a non crystalline or low crystalline form in an emulsion type composition of internal oily-solvent and external non-hydrous and water soluble solvent, whereas 1) emulsifying stabilizer comprises low fraction of the composition, and 2) emulsions of mean droplets size below one micron is obtained upon dilution with physiological fluids, and 3) facilitated dispersion of biologically active agents in body fluids is obtained, and more particularly to facilitating biological availability or improving clinical performance.

BACKGROUND OF INVENTION

The formulation of lipophilic, amphipathic, or sparingly water-soluble drugs for oral administration has proven to be difficult, since in order to be absorbed, drugs need to be solubilized in the gastro intestinal fluids which are hydrous and therefore are intrinsically not favorable medium for such insoluble bioactive molecules.

Oral drug delivery vehicles must be capable of maintaining sufficient drug concentration in a bio-available form that will enable expected absorption and biological activity. Such drug delivery vehicles must also be capable of maintaining the drug in its dissolved state and maintain stability of drug and dosage form over an extended storage period while avoiding the use of physiologically harmful solvents or excipients.

Dissolved state, which enables transport of drug from the gastro intestinal fluids into the blood circulation, is a state where single drug molecules are exists individually in the fluid medium.

One approach to overcome drugs molecules self attraction and maintain hydrophobic drugs in dissolved or solubilized state at the gastro intestinal absorptive mucous is by high surfactants content delivery systems, such as, micelles, self-emulsifying micro-emulsions and related colloidal systems.

Micelles are agglomerates of colloidal dimensions formed by amphiphilic compounds or surfactants. In aqueous solution, micelles can incorporate hydrophobic therapeutic agents in the hydrocarbon core of the micelle. Loading capacity of micelle formulations is limited by the solubility of the therapeutic agent in the micelle surfactant and dosage form is intrinsically of high surfactant ratio.

Another conventional approach is dissolving hydrophobic drugs in oily medium such as triglyceride-based solvents. This oily solution of lipophilic drug in oily phase may be further processed in two ways. One way is emulsifying in aqueous medium by the aid of surfactants, to produce an oil-in-water emulsion, which are inherently unstable dosage form, and second way is adding high amount of surfactant to produce thermodynamically stable micro-emulsions preferable self-emulsifying upon dilution in the gastrointestinal fluids. The properties of these oil-based formulations are determined by such factors as the size of the triglyceride/therapeutic agent colloidal particles and the presence or absence of surfactant additives. Size control is a significant factor affecting absorption, smaller particles resulting in better absorption.

A further disadvantage of triglyceride-containing compositions is the dependence of therapeutic agent absorption on the rate and extent of lipolysis. Although colloidal emulsion particles can transport hydrophobic therapeutic agents through the aqueous environment of the gastrointestinal tract, ultimately the triglyceride must be digested and the therapeutic agent must be released in order to be absorbed through the intestinal mucosa.

Certain surfactants commonly used in the preparation of pharmaceutical emulsions, such as polyethoxylated castor oils, may themselves act as inhibitors of lipolysis. Although recent work suggests that certain surfactant combinations, when used in combination with digestible oils in emulsion preparations, can substantially decrease the lipolysis-inhibiting effect of some common pharmaceutical surfactants (U.S. Pat. No. 5,645,856), such formulations are still subject to the other disadvantages of pharmaceutical emulsions and triglyceride-based formulations.

Example of self emulsifying system is described in U.S. Pat. No. 6,054,136 (Faraha et al). The invention relates to a composition which can be administered, in particular, orally, for pharmaceutical or cosmetic use, capable of forming a micro-emulsion in situ with the biological fluid of the body; the invention relates more especially to a composition providing of a self-micro-emulsifying carrier system for active agents, designated in the art by the English term "SMEDDS" (self-micro-emulsifying drug delivery system); these systems have the property of emulsifying in water at the temperature of the human body.

This composition as well as other self emulsifying compositions are intended, on the one hand to transport one or more soluble or sparingly soluble active agents, and on the other hand to form a micro-emulsion with the biological fluid of the human body, being understood that one or more active agents or principles in solution in a micro-emulsion has better bio-availability. However, the self emulsifying systems possess major drawback, of typical high surfactant content in the range of 20 to 50%.

High surfactant concentration may inhibit lipolysis and is disadvantageous to the intestinal mucous and has potential of causing local irritation side effects.

Thus, there is a need for pharmaceutical compositions that overcome the limitations of conventional micelle formulations, but without suffering from the disadvantages of triglyceride-containing formulations or disadvantage of high surfactant ratio.

A need therefore exists in the art of drug delivery to develop a vehicle that can be used with lipophilic and amphipathic insoluble materials, drugs or nutrients and that can be stored at various temperatures for extended periods of time and be dilutable or spontaneously mixing with an aqueous fluid such as blood or a buffer solution or gastro-intestinal fluids and deliver the drug to the absorption organ or membrane in a functional form.

In particularly, there is a need for such vehicle that will not comprise high and significant portion of surfactants that are irritating to the gastro intestinal mucous.

It is the objective of the present invention to furnish a carrier system for bioactive agents having limited water solubility, whereas an admixture to body fluid is possible or better dissolution and enhanced absorption is obtained while avoiding the side effects associated with high emulsifiers' concentration.

Unexpectedly, it has now been discovered that one: it is possible to formulate significant amount of hydrophobic water insoluble drugs in the low surfactant, oil in non-hydrous solvent, stable emulsion system composition, in a dissolved amorphous state, Two: good mixing of nano size droplets in the gastro intestinal fluids is obtained despite low surfactant concentration, and three: facilitate drug dissolution formulated with this system and four: maintaining stable amorphous or low crystalline state of drugs in the composition.

PRIOR ART

U.S. Pat. No. 6,056,971 (Goldman et al) "Method for enhancing dissolution properties of relatively insoluble dietary supplements and product incorporating same" uses high surfactant concentration 20-90 and 2-50 polyhydric alcohol; the present invention teaches lower surfactant concentration and at least 50% non-hydrous hydrophilic solvent.

U.S. Pat. No. 5,965,160 "Self-emulsifiable formulation producing an oil-in-water emulsion" (Benita at al) comprising an oily component and a surfactant which itself is not an emulsion but rather self-emulsify, become or transformed into oil-in-water emulsion upon contact with water or body fluids. In contrast, the present invention composition is an emulsion itself, as is, before mixing with water and therefore a different physical form.

U.S. Pat. No. 5,993,858 "Method and formulation for increasing the bioavailability of poorly water-soluble drugs" (Amidon et al) a self-microemulsifying excipient formulation for increasing the bioavailability of a drug" "the range of concentration of the surfactant/co-surfactant broadly ranges from 15 to 90% (v/v) and more preferably ranges from approximately from 45% to 55% (v/v)." The present invention teaches much lower, about one tenth, surfactant concentration.

U.S. Pat. No. 6,096,338 (Lacy et al) is a "Delivery systems for hydrophobic drugs" that comprises 30-45% by weight of said hydrophilic surfactant component, and 20-40% by weight of said lipophilic surfactant component. "a hydrophilic surfactant component which substantially inhibits the in vivo livolysis of said digestible oil". "The carrier comprises a digestible oil and a pharmaceutically acceptable surfactant component for dispersing the oil in vivo upon administration of the carrier". In contrast, the present invention carrier is a real emulsion and comprises about one tenth surfactant concentration, while maintaining good mixing with physiological fluids.

U.S. Pat. No. 6,140,375 (Nagahama et al) is a "Microemulsions" states that "The components of the pharmaceutical compositions of the present invention in amounts such that upon dilution with an aqueous solution, the composition forms a clear, aqueous dispersion." "The particle sizes in the aqueous dispersions of the present invention are much smaller than the larger particles characteristic of vesicular, emulsion or microemulsion phases." In contrast, the present invention forms turbid emulsions upon dilution with water or body fluids differently from the above which is characterized by high surfactant concentration that form clear solution upon dilution with water.

Following patents comprising high surfactant content; U.S. Pat. No. 6,309,665 (Barthelemy et al) "Composition with sustained release of active principle, capable of forming a microemulsion" and U.S. Pat. No. 6,312,704 (Farah et al) "Orally administrable composition capable of providing enhanced bioavailability when ingested" The systems are "a system which is self-microemulsifying on contact with a hydrophilic phase provided, after ingestion, by physiological fluid".

U.S. Pat. No. 6,383,471 (Lipocine corp.) also teaches high ratio surfactants compositions, typically from 30% to 80% surfactant content in "Compositions and methods for improved delivery of ionizable hydrophobic therapeutic agents". Such compositions are not emulsions and no reference to particle size is made.

SUMMARY OF THE INVENTION

According to the present invention there is provided a pharmaceutical or nutritional composition in the form of an non-hydrous emulsion with mean droplet size below one micron, comprising at least one low solubility bioactive compound that is dissolved, solubilized or dispersed in a non crystalline or low crystalline form in the composition, at least one oily solvent comprising an internal phase, at least one emulsifying stabilizer, in a significant low concentration, and a continuous non-hydrous and hydrophilic external phase wherein said composition is easily mixed with body fluids to form homogeneous dispersion with mean particle size of less than one micron and improved solubilizing and dissolution of drug is obtained.

Thus, in one embodiment, this invention comprises an admixture of a pharmacologically active agent having low or poor water solubility formulated in a non-hydrous emulsion, and in none or low crystalline molecular form for the administration of therapeutically effective amounts of said active agent.

In another embodiment, the invention provides a method for enhancing the dissolution and oral availability of a pharmacologically active agent having low or poor water solubility, wherein the method comprises oral administering of the patient undergoing treatment a mixture of the pharmacologically active agent in the solubilizing and dissolution facilitating composition as described herein.

It has been unexpectedly found that despite low emulsifying stabilizer concentration used in the current invention composition, fast and stable dissolution of sub micron droplets is obtained upon dilution with biological fluids and also it has been found that less energy, time and pressure is required to obtain small and uniform particle size for emulsion systems of oil in non-hydrous composition.

It has been unexpectedly found that despite low emulsifying stabilizer concentration used in the current invention composition, adequate solubilization and molecular dispersion of low solubility drugs is obtained and re-crystallization rate is highly suppressed.

DETAILED DESCRIPTION OF THE INVENTION

The present invention provides in one aspect a composition comprising an oil in non-hydrous hydrophilic solvent emulsion with mean droplet size below one micron, comprising: (1) a poor or low-solubility drug dissolved or dispersed in the composition, whereas all or majority of drug is non crystalline, and (2) At least one oily solvent comprising the internal phase of the emulsion, and (3) at least one emulsifying stabilizer, whereas the emulsifying stabilizer content in the final composition is low, typically below 10%, and (4) a continuous non-hydrous and hydrophilic phase, wherein enhanced solubilizing effect of bioactive compound in biological fluids is obtained.

In another aspect, the invention comprises an emulsion of oil in non-hydrous composition, wherein the emulsifier stabilizer is present in a small but sufficient amount so that the composition is stable at room temperature and also facilitates the dissolution of the drug or nutrient at the target organ fluids environment relative to an appropriate control composition. In yet another aspect, the invention provides a method for co-administering a low or poor solubility drug dissolved or dispersed in the composition, whereas majority of drug is not crystalline and do not re-crystallize or only slightly crystallize upon storage.

The Drug

Compositions of the present invention are preferred for low-solubility drugs having a solubility of less than 10 mg/mL, more preferred for low-solubility drugs having a solubility of less than 1 mg/mL, and even more preferred for low-solubility drugs having a solubility of less than 0.1 mg/mL.

The meaning of "low-solubility drug," is that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL.

The term "drug" or "pharmacologically active agent" or "bioactive agent" as used herein is intended to mean a compound or composition of matter which, when administered to an organism (human or animal) induces a desired pharmacological and/or physiologic effect by local and/or systemic action. In general, the terms include the therapeutic or prophylactic agents in all major therapeutic or prophylactic areas of medicine. A bioactive agent may be a phyto-chemical, drug, nutrition agent, Vitamin, peptide, oligonucleotide or liposaccharide or combinations thereof.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein inhibitors.

The present invention is useful with any drug capable of being formulated as an amorphous drug. The term "drug" is conventional, denoting a compound having beneficial prophylactic and/or therapeutic properties when administered to an animal, especially humans. The drug does not need to be a low-solubility drug in order to benefit from this invention, although low-solubility drugs represent a preferred class for use with the invention. Even a drug that nonetheless exhibits appreciable solubility in the desired environment of use can benefit from the increased solubility/bioavailability made possible by this invention if the formulation and administration in the presented carrier can reduce the size of the dose needed for therapeutic efficacy or increase the rate of drug absorption in cases where a rapid onset of the drug's effectiveness is desired.

The active agent may be any agent that is traditionally used as a medicament and lends itself to being administered through the oral cavity. Such active agents may be vitamins, chemotherapeutics; antimycotics; oral contraceptives, nicotine or nicotine replacement agents, minerals, analgesics, antacids, muscle relaxants, antihistamines, decongestants, anesthetics, antitussives, diuretics, anti-inflammatories, antibiotics, antivirals, psychotherapeutic agents, anti-diabetic agents and cardiovascular agents, nutraceuticals and nutritional supplements.

Vitamins and co-enzymes that may be delivered using this invention include but are not limited to water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs, vitamin A and the carotenoids, retinoic acid, vitamin E and vitamin K and Coenzyme Q10.

Example of botanical bioactive agents, are: polyphenols, isoflavones, resveratrol, soy isoflavones, grape seed extract polyphenols, curcumin, epigenin. Anti-inflammatory plant extracts such as aloe vera, echinacea and chamomile hammamelis extracts, anti-psoriatic such as chinese zizipus jujuba. Astringents such as hammamelis anti bacterial such as artemisia, chamomile, golden seal. Immune modulators such as echinacea, anti-aging or anti-cancer or anti-photo damage, anti-inflammatory such as feverfew parthenolides, rejuvenation agents, carotenoids, beta-carotene, lycopene, astaxanthons, lutein, tocopheryl and retinol.

Coronary drugs: including vasodilators such as nitroglycerin, isosorbide dinitrate, Calcium-antagonists such as verapamile, nifedipine and diltiazem, Cardiac-glycosides such as digoxine. Analgesics: eg. morphine, buprenorphine, etc; Local anaesthetics: eg. lidocaine, etc;

Example of cholesterol and triglycerides lowering drug: fenofibrate, lovastatin, simvastatin, pravastatin, fluvastatin, atorvastatin, or cerivastatin.

Anxiolytics, sedatives & hypnotics: diazepam, nitrazepam, flurazepam, estazolam, flunitrazepam, triazolam, alprazolam, midazolam, temazepam, lormetazepam, brotizolam, clobazam, clonazepam, lorazepam, oxazepam, buspirone, etc; Migraine relieving agents: sumatriptan, ergotamines and derivatives etc; Drugs against motion sickness: eg. cinnarizine, anti-histamines, etc; Anti-emetics: eg. ondansetron, tropisetron, granisetrone, metoclopramide, etc. Others: such as disulfuram, vitamin K, etc.

Examples of chemotherapeutics agents include but are not limited to cisplatin (CDDP), procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Example of antibiotics drugs: Tetracyclines such as tetracycline, doxycycline, oxytetracycline, chloramphenicol etc; Macrolides such as erythromycin and derivatives, etc; Antivirals: such as acyclovir, idoxuridine, tromantadine etc; Antimycotics: Miconazole, ketoconazole, fluconazole, itraconazole, econazole, terconazole, griseofulvin, and polyenes such as amphotericin B or nystatine etc; Anti-amoebics: Metronidazole, metronidazole benzoate and tinidazole etc; Anti-inflammatory drugs: steroids or NSAID's such as indomethacin, ibuprofen, piroxicam, diclofenac etc; Anti-allergics: Disodium cromoglycate etc; Immunosuppressive agents: cyclosporins etc;

Antimicrobial agents that may be used include but are not limited to naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, .beta.-lactamase inhibitors; meziocillin, piperacillin, aztreonam, norfloxacin, trimethoprim, ceftazidime, ceftriaxone and dapsone.

Antifungal agents that may be delivered include but are not limited to ketoconazole, fluconazole, nystatin, itraconazole, clomitrazole, and amphotericin B. Antiviral agents that may be used include but are not limited to acyclovir, trifluridine, idoxorudine, foscarnet, ganciclovir, zidovudine, dideoxycytosine, dideoxyinosine, stavudine, famciclovir, didanosine, zalcitabine, rifimantadine, and cytokines.

Antihistamines are represented by but are not limited to cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prilamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine.

Decongestants and antitussives include agents such as dextromethorphan, levopropoxyphene napsylate, noscapine, carbetapentane, caramiphen, chlophedianol, pseudoephedrine hydrochloride, diphenhydramine, glaucine, pholcodine, and benzonatate.

Anesthetics include etomidate, ketamine, propofol, and benodiazapines (e.g., chlordiazepoxide, diazepam, clorezepate, halazepam, flurazepam, quazepam, estazolam, triazolam, alprozolm, midazolam, temazepam, oxazepam, lorazepam), benzocaine, dyclonine, bupivacaine, etidocaine, lidocaine, mepivacaine, promoxine, prilocalne, procaine, proparcaine, ropivacaine, tetracaine. Other useful agents may include amobartital, aprobarbital, butabarbital, butalbital mephobarbital, methohexital, pentobarbital, phenobarbital, secobarbital, thiopental, paral, chloral hydrate, etchlorvynol, clutethimide, methprylon, ethinamate, and meprobamate.

Analgesics, include opioids such as morphine, mepidine, dentanyl, sufentranil, alfentanil, aspirin, acetaminophen, ibuprofen, indomethacine, naproxen, atrin, isocome, midrin, axotal, firinal, phrenilin, ergot and ergot derivatives (wigraine, cafergot, ergostat, ergomar, dihydroergotamine), imitrex.

Diuretics include but are not limited to acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, amiloride, triamterene, sprionolactone, canrenone, and potassium canrenoate.

Anti-inflammatories include but are not limited to salicylic acid derivatives (e.g. aspirin) paraminophenol derivative (e.g. acetaminophen) indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone).

Psychotherapeutic agents include thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, eldepryl.

Cardiovascular agents include but are not limited to nitroglycerin, isosorbide dinitrate, sodium nitroprisside, captopril, enalapril, enalaprilat, quinapril, lisinopril, ramipril, losartan, aminone, lirinone, vesnerinone, hydralazine, nicorandil, prozasin, doxazosin, bunazosin, tamulosin, yohimbine, propanolol, metoprolol, nadolol, atenolol, timolol, esmolol, pindolol, acebutolol, labetalol, phentolamine, carvedilol, bucindolol, verapamil, nifedipine, amlodipine and dobutamine.

Semi-Solid or Viscous Liquid Drug-Containing Composition

The drug is present in the composition in a molecular dispersion comprising a low-solubility drug and a semi-solid matrix. At least a major portion of the drug in the dispersion is amorphous. The term "a major portion" of the drug means that at least 60% of the drug is in amorphous form, rather than a crystalline form. Preferably, the drug in the dispersion is substantially amorphous. As used herein, "substantially amorphous" means that the amount of the drug in amorphous form is at least 80%. More preferably, the drug in the dispersion is "almost completely amorphous" meaning that the amount of drug in the amorphous form is at least 90% as measured by X-ray diffraction or differential scanning calorimetry ("DSC"), or any other standard quantitative measurement.

The amorphous bioactive agent exists in the semi-solid or viscous liquid drug/matrix as a solution or solid solution or co-precipitate, where the drug is homogeneously distributed through the dispersion or a portion of the drug may exist in relatively drug-rich domains. Preferably, the dispersion is substantially homogeneous so that the amorphous drug is dispersed as homogeneously as possible throughout the dispersion. As used herein, "substantially homogeneous" means that the amount of the drug presents in drug-rich amorphous domains within the dispersion is less than 20%. Preferably, the dispersion is "completely homogeneous," meaning that the amount of drug in drug-rich domains is less than 10%.

An amorphous compound has a higher energy level than a crystalline compound; therefore, a solid will be more soluble in the amorphous state than in the crystalline state. Improved solubility will lead to rapid and more complete dissolution, and in the case of a poorly soluble drug substance, improved bioavailability.

The Oily Solvent Comprising the Internal Phase

Oily solvent is any pharmaceutical or food approved substance which is oily in its nature that is not mixing or dissolving with water or hydrous mediums. Such oily solvent may be natural or synthetic or semi-synthetic, in the form of liquid, semi-solid or solid at room temperature.

Example of oily solvents are mineral oil, vegetable oil, silicon oil, lanolin, refined animal oil, hydrocarbon esters derived from vegetable animal or marine origin.

Example of vegetable oils are: isopropyl miristate, jojoba oil, almond oil, avocado oil, coconut oil, capric-caprylic tryglyceride of fractionated coconut oil, nutmeg oil, castor oil, olive oil and oleic acid, soybean oil, sunflower oil, canola oil etc. The oil may be saponifiable or unsaponifiable and liquid or solid at room temperature.

Special oils are essential oils or poly unsaturated fatty acid or oils or etherified oils and modified semi-synthetic oils. Example of semi-synthetic oil is a product of inter-esterification of hydrogenated palm oil palm kernel oil ($C_8$-$C_{18}$ triglycerides) with melting point at 30° C.-50° C.

A further preferred class of hydrophobic solvents may be selected from the groupf comprising isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, glyceryl oleate, tocopheryl linoleate, wheat germ glycerides, arachidyl propionate, myristyl lactate, isopropyl palmitate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristal myristate, isocetyl stearate and isoadipate.

A further class are fatty acids include, but are not limited to, caproic acid, capric acid, caprylic acid, oleic acid, palmoic acid, stearic acid, linoleic acid, octanoic acid, decanoic acid, linolenic acid, palmitic acid, palmitoleic acid, arachidic acid, myristic acid, behenic acid and lignic acid, or fatty alcohols, and also mono and diglycerides.

The Emulsifying Stabilizer

The emulsifying stabilizer is any surface active agent of pharmaceutical cosmetic or food grade that has an amphiphilic nature and that is able to stabilize the emulsion. The surfactant can by hydrophilic, hydrophobic, or a mixture of hydrophilic and hydrophobic surfactants.

Examples are Polyethoxylated Fatty Acids, PEG-Fatty Acid Diesters, EG-Fatty Acid Mono- and Di-ester Mixtures, Polyethylene Glycol Glycerol Fatty Acid Esters, Alcohol-Oil Transesterification Products, Polyglycerized Fatty Acids, Propylene Glycol Fatty Acid Esters, Mixtures of Propylene Glycol Esters-Glycerol Esters, Mono- and Diglycerides, Sterol and Sterol Derivatives, Polyethylene Glycol Sorbitan Fatty Acid Esters, Polyethylene Glycol Alkyl Ethers, Sugar Esters, Polyethylene Glycol Alkyl Phenols, Polyoxyethylene-Polyoxypropylene Block Copolymers, Sorbitan Fatty Acid Esters, Ionic Surfactants.

Preferred stabilizing emulsifiers are non-ionic and PEG free surface active agents, such as: non ionic condensate of a carbohydrate and fatty acid, such as; Sucrose esters of fatty acids and Glucosides of fatty acids and Sorbitan esters of fatty acids, various esters of mono- and diglycerides of fatty acids and sucroglycerides, Ascorbic acid esters, Glycerin esters, cetearyl glucosides, Polyacids carbohydrate esters of fatty acids, Citric acid esters of fatty acids, and the colloidal gums and the like.

Further examples of preferred emulsifying stabilizers are polyglyceryl fatty acids esters such as Polyglyceryl-10-fatty acid, for example; Polyglyceryl-10-tetralinoleate or Polyglyceryl-10-oleate or Polyglyceryl-10-stearate or Polyglyceryl-10-laurate.

Further examples of preferred emulsifying stabilizers are amphiphylic polymers such cellulose derivatives (methyl cellulose, hydroxylpropyl cellulose, hydroxylpropyl methyl cellulose, ethyl cellulose), and acrylate derivatives such as Pemulene® types from BFGoodrich USA. Also colloidal silica or natural gums such as, Xanthan gum and microcrystalline cellulose and microcrystalline cellulose blends with sodium carboxymethyl cellulose are practical emulsifiers stabilizing agents.

Preferred sucrose esters are sucrose stearate and sucrose palmitate (Sisterna SP50 and SP50C or Sisterna SP70) that are blends with free mono esters. Preferred HLB of surfactants emulsifying stabilizers is 6 to 18 and more preferably 10 to 15.

Low Surfactant Ratio

It has been found that low concentration of emulsifier stabilizer is practically applied to obtain required shelf life stability and obtain and maintain below one micron mean particle size. Typical low surfactant ration is below 20%, preferably below 10% and more preferably below 5% and more preferably from 1% to 5%.

In contrast to significant load of surfactants in "Self Emulsifying Delivery Systems", in the range of 20% to 50%, it has been unexpectedly discovered that low surfactant ration compositions maintain sub-micron or nano-size mean oil globules size when diluted with physiological fluids such as gastrointestinal content or simulated content. The nano-size mean globule diameter is maintained for the period relevant for physiological drug absorption and for the relevant pH and physiological conditions of gastro intestine system.

Also, it has been discovered, that it is possible to obtain nano-size droplets following dilution with body fluids without use of polyoxyethylene derivative surfactants and without use of blends surfactants (complex emulgators) required to obtain "Self Emulsifying Delivery Systems".

The Continuous Non-Hydrous and Hydrophilic Phase

The continuous non-hydrous and hydrophilic phase is made of organic solvents that are completely and immediately miscible with water and physiological fluids Preferred pharmaceutically acceptable water-miscible non-aqueous solvents suitable for use in the non-aqueous compositions of this invention include, but are not limited to, glycols such as propylene glycol and glycerin, polyethylene glycols of various molecular weights and the like and their mixtures.

Less preferable are organic solvents that are only moderately or partially miscible with water.

Example of other preferred solvents and possible co-solvents are: polyols or amides or esters, butanediols and isomers thereof, pentaerythritol, sorbitol, mannitol, dimethyl isosorbide, polypropylene glycol, ethers of polyethylene glycols having an average molecular weight of about 200 to about 6000, such as tetrahydrofurfuryl alcohol PEG or methoxy PEG; Amides, such as 2-pyrrolidone, 2-piperidone, $\epsilon$-caprolactam, N-alkylpyrrolidone, N-hydroxyalkylpyrrolidone, N-alkylpiperidone, N-alkylcaprolactam, dimethylacetamide; Esters, such as ethyl propionate, tributylcitrate, acetyl triethylcitrate, acetyl tributyl citrate, triethylcitrate, ethyl butyrate, triacetin, propylene glycol diacetate, .epsilon.-caprolactone and isomers thereof, .delta.-valerolactone and isomers thereof, .beta.-butyrolactone and isomers thereof; and other solubilizers known in the art, such as dimethyl acetamide, dimethyl isosorbide, N-methylpyrrolidones, transcutol. Mixtures and any combination of above solvents are most preferable.

Excipients and Additives

The oily solvent in non-hydrous emulsion composition may further comprise excipients or inactive ingredients or additives, such as stabilizers, colorants, polymers, antioxidants, flavoring and fragrance, neutralizing agents and fillers.

The term "polymeric" is used conventionally, meaning a compound that is made of monomers connected together to form a larger molecule. A polymeric component generally consists of at least about 20 monomers. Thus, the molecular weight of a polymeric component will generally be about 2000 daltons or more. Polymeric matrix components generally will result in dispersions with improved concentration enhancement relative to non-polymeric matrix components. Exemplary polymeric components for use as the additives include polyethylene glycols, polyoxyethylene glycols, polyethylene-propylene glycol copolymers, polyethylene oxides, polyvinyl pyrrolidinone (also referred to as polyvinyl pyrrolidone or povidone or PVP), polyvinyl alcohol, polyethylene-vinyl alcohol copolymers, polyvinyl alcohol polyvinyl acetate copolymers, xanthan gum, carrageenan, pullulan, zein, hydroxypropyl cellulose, hydroxypropyl methyl cellulose, carboxy methyl cellulose, carboxylic acid-functionalized polymethacrylates, amine-functionalized polymethacrylates, chitosan, chitin, polydextrose, dextrin and starch. Also included within this definition are high molecular weight proteins such as gelatin and albumin.

The polymers may be bioadhesive polymers coating, positively charged polymers, or matrix forming for slow release polymers. The present composition may be further entrapped in such bioarodible matrix for slow release or bioadhesive or charged polymers Dosage Forms The resulting composition of current invention, comprising the low solubility bioactive agent, may be dosed directly for oral administration, diluted into an appropriate vehicle for oral administration, filled into capsules, or delivered by some other means obvious to those skilled in the art. The composition may be liquid or semi-solid at room temperature and liquid or semi-solid at elevated temperature such as body temperature.

Preferred consistency of the composition is viscous liquid or semi-solid at room temperature, with viscosity of at least 1,000 cps and preferably above 5,000 cps. Preferred consistency is plastic or pseudo-plastic more preferably with no or low yield value.

Preferred dosage forms are soft gelatin capsule or hard vegetable capsules. More preferable are vegetable caps made of vegetable origin polymers instead of animal origin gelatin caps. Dosage forms may be coated or enteric-coated and shaped into many sizes and shapes.

The delivery system of the present invention results in facilitated solubilization and can be used to improve the oral bioavailability and solubility of said bioactive agent, or for safe systemic administration of difficult to formulate drugs. Preferred injectable dosage form is produced sterile in vial for dilution before use and is passed through 5 or 2 micron filter in line of infusion device.

The semi-solid composition is also suitable for topical application of dermatological or cosmetic bioactive agents that tend to crystallize upon storage and hence, loose activity. Stabilizing low solubility topical drugs in a solubilized state in the semi-solid matrix enables preserving drug activity upon storage or increase drug absorption over its crystalline state.

Preparation of Compositions

The current invention, non-aqueous nano delivery system production process involves two basic consecutive steps; the first is the preparing the oily solvent phase comprising the bioactive agent by solubilizing or dissolving a liquid or solid drug in the oily solvent phase until homogeneity is obtained, and the second step is the emulsification and homogenizing process of the oil phase with the hydrophilic and non-aqueous phase.

Bioactive agents with high melting point are co-melted in the oily solvent alone or with solubilizing agents, the emulsifying stabilizer or co-solvents on warm water or on hot oil bath when above 100° C. is required. First step in the production of nano non-aqueous emulsion of the present invention is selection of appropriate oily solvent to dissolve the hydrophobic drug. Selection of various co-solvents and emulsifying stabilizer is also a part of the oily solvent phase production and hydrophobic drug incorporation in a molecular uniform dissolved state.

Alternatively, the bioactive agent is dissolved with the oily solvent in a suitable organic solvent and organic solvent is evaporated and mixture is emulsified in the non-aqueous solvent with the aid of the emulsifying stabilizer. Heating and temperatures are a consequence of used oily solvent and emulsifying stabilizer composition. It is necessary to co melt the ingredients and heat different phase. However, it is also possible to heat only one phase, internal or external, as well as applying modern cold emulsification methods. Many hydrophobic drugs with high melting point, such as above 200° C., are lending themselves to co-melt with well selected oily solvent mixture at much lower temperature relative to their melting point.

The bioactive agent is dissolved in the oily solvent mixture is added and vigorously mixed into the non-hydrous and hydrophilic solvents and selected emulsifying stabilizer.

The non-aqueous and hydrophilic phase is composed of such ingredients that are viscous liquid at the time of emulsification and preferably of much increased viscosity when cooled to ambient temperature. Preferred examples are glycerin, polyethylene glycols such as Macrogol-1500 or mixtures of liquid and solid Macrogols to obtain desired viscosity profile, for example: liquid Macrogol-600 with solid Macrogol-4000. Selective mixtures of Macrogols will also affect drug release kinetics and it is a tool by the hand of skill in the art to influence dissolution rate and pharmacokinetics.

Low viscosity non-aqueous solvents will preferably be mixed with solidifying agents such as gelling agents to obtain desired viscosity and semi-solid state of final product.

In a preferred embodiment, the process of producing the non aqueous emulsion composition is by co-melting the hydrophobic drug with oily solvent and emulsifying stabilizer and co-solubilizer where needed, until clear solution is obtained. The clear solution is examined under light microscope for absence of crystals or solid distinct areas. The hydrophilic non-aqueous external phase composition is heated to 90° C.-100° C. and slowly added under vigorous mixing to the hot oil phase and removed from heat source and cooled. The homogenization is performed while mixture is liquid and before and until solidifying while cooling to room temperature.

Emulsification equipment for producing oil in non hydrous emulsions does not differ from the equipment used for preparing emulsions, lotions or dispersion system in the pharmaceutical or cosmetic industry and is typically, mixers, homogenizers, colloidal mills, pressure homogenizers, rotary blenders, etc. Special equipment such as micro-fluidizer or high pressure homogenizer may be used.

In preferred embodiments of the present invention the following quantities are preferable:

a) Said oily solvent is present in an amount ranging from about 1-40 wt/wt %, more preferable from 2-20 wt/wt %; and b) said emulsifying stabilizer is present in an amount ranging from about 0.1-20 wt/wt %, or from about 0.1-5 wt/wt %; and c) said low or poor water insoluble bioactive component is present in an amount ranging from about 0.1-20 wt/wt %.

A preferred embodiment of the present invention is the following process for producing homogeneous amorphous dispersion of hydrophobic drug in non-aqueous nano size droplets semi-solid emulsion;

A—Heating and co-melting the drug and selected oils and emulsifying stabilizers until clear solution devoid of solid material is obtained.

B—Heating non-aqueous hydrophilic phase to 80° C.-100° C.

C—Adding the hot non-aqueous phase (B) to hot oily phase (A) in increments under stirring and mixing.

D—Homogenizing the emulsion (C) until the hot liquids cools into semi-solid state.

The composition is suitable for filling in soft gelatin capsules and selected vegetable capsules and filling process is preferably performed while composition is soft, not cooled to room temperature.

In a most preferred embodiment said emulsifying stabilizer is biodegradable (i.e., degradable in the human body and the environment) and is substantially free of polyoxyethylene and does not inhibit lipolysis and is preferably of botanical origin.

In an even further preferred embodiment of the present invention said non-aqueous solvent constitutes a continuous phase of said emulsion and a minor portion of water is included in said phase.

In a preferred aspect of the invention, the combination of an oil-in-non-hydrous solvent forms an emulsion that facilitates the dispersion and dissolution of a water insoluble bioactive component or drug, in a biocompatible, safe and convenient dosage form.

As will be realized, the present invention provides an emulsion which is produced alcohol and/or water free, has a prolonged shelf life and improved heat stability for withstanding elevated temperatures during a long period of time. Furthermore, the oil-in-anhydrous solvent emulsion resists sub-zero temperatures; it is stable upon freezing and does not break at minus 20° C. Thaw of oil-in-non-hydrous emulsions is simple and does not affect original properties.

Oil-in-anhydrous solvent emulsions are easily prepared. It is possible, to produce coarse oil-in-anhydrous solvent emulsions of 5 to 10 microns droplet size with simple stirring and without resort to the use of high shear mixers. It is also easy to control droplet size by the utilization of appropriate mixing equipment and energy input. Fine oil-in-anhydrous solvent emulsions, having a mean droplet size of below one micron, are achieved with a conventional homogenizer or "Silverson" type mixer at moderate to high speed and a short duration of mixing. High shear homogenizer mixing is sufficient to obtain emulsions containing 0.5 to 1 microns mean droplets size, consequent high pressure homogenization produces 0.5 to 0.1 mean particle size. Mean droplet size depends also on specific formula and selection of emulsification equipment is done by skill in the art.

Oil-in-anhydrous solvent emulsions may be prepared in various hot or cold methods. In hot method, the oily and anhydrous solvent phases are heated separately to 80° C. until all ingredients melt and are well dissolved. The phases are combined while mixing. Mixing may be performed with any mixer, blender, homogenizer, etc. which is used for producing emulsions. Oil-in-non-hydrous emulsions may also be prepared by heating all the ingredients, including oil, non-hydrous solvent and emulsifying stabilizers in a single batch, heating to achieve melting of solids and with continued mixing to promote emulsification until cooled to room temperature.

The bioactive agent is co-melted in the oily phase. The oily phase is formulated to specifically dissolve the hydrophobic bioactive agent. Method for facilitating the dissolution or solubilization of the bioactive agent in the oily phase are for example; use of organic solvent such as ethanol which is later evaporated, co-emulsifiers preferably of low HLB, oily co-solvents such as fatty esters, isopropyl miristate or isoadipate, described above in the oily solvent agents list, phospholipids and/or heating to high temperature for short period. The bioactive agent or drug may be formulated during and as part of the emulsion production or introduced into ready emulsion composition with or without further heating.

If solvent is used, suitable solvents include, for example, lower alkyl alcohols such as methanol, ethanol, or any other pharmaceutically-acceptable organic solvent in which the low solubility bioactive agent and the oily solvent have appreciable solubility.

Care should be taken to avoid re-crystallization of bioactive agents tending for re-crystallization, by adding crystallization inhibiting agents such as viscosity modifiers, salts, complexion agents such as polymers or co-solvents such as dimethyl isosorbide and others listed above. Inhibition of re-crystallization where needed is tailored for each drug by skill in the art.

Typical oil-in-anhydrous solvent emulsions are characterized by having viscosity of 10,000 to 100,000 centipoise and newtonian flow at ambient temperature. Viscosity may be reduced by the addition of water. The oil-in-anhydrous solvent emulsion viscosity may be controlled by addition of viscosity forming agents, such as, carbomers, carbopol, cellulose derivatives or natural gums, such as xanthan gum or colloidal fumed silica. Also, non Newtonian characteristics are easily achieved by the same additives.

Oil-in-anhydrous solvent emulsions are suitable for use in humans and animals, oral, rectal, vaginal, topical, and transdermal applications. I.V., I.M. S.C. or other form of injection is possible following preparative dilution step, before the administration, with physiological fluid such as saline or sucrose sterile solution, to obtain physiologically acceptable sterile and isotonic product.

The invention is thus, in one embodiment, a method for facilitating the magnitude or rate of absorption of a pharmacologically active agent through the gastro intestinal mucous, wherein the method involves co-administration of the selected agent in a solubilization enhancer composition comprising oil in anhydrous solvent emulsion.

Mixing with Physiological Fluids

Dilution of said composition in simulated gastric or intestinal fluids result in fast and complete dispersion and oil-in-water type emulsion is obtained with mean droplet size below one micron, and hazy translucent appearance. Dissolution test as described in USP may reveal much faster and complete dissolution; however there is no real solubility of the low solubility drug in the medium, but solubilization. No crystals are observed under light microscope for a period sufficient for drug absorption.

Dilution of said composition with isotonic aqueous sterile solution for injection, available in clinics and hospital, also results in sub micron type oil in water product that is safe for parental I.V. administration. It is possible to dilute said composition in a simple setup and obtain non hemolytic formula due to is-tonicity and very low surfactants concentration in said composition and much lower following dilution.

Terminology

Mean droplet size below one micron or "sub-micron" or "nano-size" as is used herein relates to practical mean droplet size in the range of few to 1,000 nanometers.

The term HLB is an arbitrary scale from 0 to 40 depicting the Hydrophilic/Lipophilic Balance of a surfactant. Products with low HLB are more oil soluble. High HLB represents good water solubility. Note that HLB is a numerically calculated number based on the surfactants molecular structure. It is not a measured parameter.

The term anhydrous and non-hydrous and Nonaqueous are interchangeable and describe a non water or non aqueous medium.

The term "bioactive agent" is any compound of synthetic or natural origin, drug or nutrient, small or large molecule that exerts beneficial biological activity on mammalian body.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

Lovastatin or Atrovastatin Composition

| INGREDIENT | % w/w |
|---|---|
| Lovastatin | 2.0 |
| Caprylic/Capric triglyceride | 8.0 |
| Sucrose ester | 4.0 |
| Glyceryl monostearate | 2.0 |
| Glycerin | To 100 |

Caprylic/Capric triglyceride (MCT oil) sucrose ester and glyceryl monostearate are heated to 80° C. and co-melted. Lovastatin is added and mixture is heated until co-melted. Glycerin heated to 80° C. is added and composition is homogenized and cooled to room temperature and filled in hard vegetable caps and evaluated for stability at 40° C. and 5° C. Lovastatin is well solubilized in this composition and no original crystals are observed in the composition following one month storage at 5° C.

Mean particle size upon dilution and gentle swirling in simulated gastric fluids (SGF) or simulated intestinal fluids (SIF) is below one micron and remains sub-micron for couple of hours post dilution.

Example 2

Lycopene or Astaxanthin Composition

| INGREDIENT | % w/w |
|---|---|
| Lycopene | 20.0 |
| Caprylic/Capric triglyceride | 20.0 |
| Sucrose ester | 5.0 |
| Glyceryl monostearate | 5.0 |
| Glycerin | To 100 |

The Lycopene and Sucrose ester are heated on hot oil bath until co-melted and no Lycopene crystals are detected. The MCT oil is heated to 80° C. and added to Lycopene/sucrose ester mixture under vigorous mixing. Mixing is continued until mixture is cooled to 80° C. Glycerin is added under vigorous mixing and composition is cooled to room temperature under high shear mixing. Major part of Lycopene, about 80% is solubilized in the oily phase and major part of the Lycopene is amorphous and do not re-crystallize to original typical crystals following six months storage at ambient temperature.

Upon dilution with simulated gastric fluids (SGF) or simulated intestinal fluids (SIF) there is obtained oil-in-water emulsion with mean particle size below one micron.

Example 3

Lycopene or Astaxanthin Composition

| INGREDIENT | % w/w |
|---|---|
| Lycopene | 14.0 |
| Caprylic/Capric triglyceride | 8.0 |
| Triacetin | 8.0 |
| Sucrose ester | 8.0 |
| Glycerin | To 100 |

Example 4

Coenzyme Q10 Composition

| INGREDIENT | % w/w |
|---|---|
| Coenzyme Q10 | 15.0 |
| Caprylic/Capric triglyceride | 8.0 |
| Lecithin | 8.0 |
| Hydrogenated palm oil hard fats | 4.0 |
| Sucrose ester | 2.0 |
| Macrogol 4000 | 30.0 |
| Macrogol 400 | To 100 |

Coenzyme Q10 is co-melted with Caprylic/Capric triglyceride, Sucrose ester and Lecithin at 70° C. and Propylene glycol pre-dispersed with PVP is added and mixture is homogenized until submicron droplets size is obtained.

Example 5

Indomethacin Composition

| INGREDIENT | % w/w |
|---|---|
| Indomethacin | 5.0 |
| Caprylic/Capric triglyceride | 10.0 |
| Glycryl monostearte | 1.0 |
| Sucrose ester | 4.0 |
| Polyvinyl pyrrolidone K90 | 0.2 |
| Glycerin | To 100 |

Indomethacin, Caprylic/Capric triglyceride, Glyceryl monostearte and Sucrose ester are mixed together and heated until co-melted and emulsified in glycerin mixture and pre dispersed PVP. Mean particle size of 400 nanometers is obtained.

Example 6

Benzodiazepine Composition

| INGREDIENT | % w/w |
|---|---|
| Benzodiazepine | 1.0 |
| Caprylic/Capric triglyceride (MCT oil) | 8.0 |
| Sucrose ester | 4.0 |
| Polyvinyl pyrolidone K90 | 0.4 |
| Macrogol 4000 | 35.0 |
| Macrogol 400 | To 100 |

Benzodiazepine is co-melted on oil bath with the MCT oil and Arlacel 481. Other ingredient are mixed and heated separately to 80° C. and added slowly to Hydrocortisone and MCT oil phase under vigorous mixing. Mixture is then homogenized with high shear homogenizer to obtain sub micron droplet size.

Example 7

Nifedipine Composition

| INGREDIENT | % w/w |
|---|---|
| Nifedipine | 6.0 |
| Caprylic/Capric triglyceride | 12.0 |
| Stearic acid | 2.0 |
| Pemulene TR2 | 0.2 |
| Triethanolamine | 0.05 |
| Sorbitan monostearate | 2.0 |
| Sorbitan tristearate | 2.0 |
| Macrogol 4000 | 12.0 |
| Macrogol 400 | To 100 |

Nifedipine mixture with Caprylic/Capric triglyceride, Stearic acid and sorbitans is heated in microwave oven until co-melted and clear solution is obtained. All other ingredients are mixed and heated on hot plate to 70° C. and added slowly and under vigorous mixing into Nifedipine oil phase. 100 grams of emulsion is removed from heat source and homogenizing while cooling with an ultra-turax type high shear homogenizer for one minute. The composition is left to cool slowly at ambient temperature.

Example 8

Piroxicam Composition

| INGREDIENT | % w/w |
|---|---|
| Piroxicam | 10.0 |
| Triacetin | 10.0 |
| Sucrose ester | 2.0 |
| Glyceryl nonostearate | 2.0 |
| Stearic acid | 2.0 |
| Glycerin | To 100 |

Homogenizing is performed with ultra-turax type high shear homogenizer. Mean droplet size of semi-solid composition of example 7 was measured with photon correlation spectrometry; 600 nanometers mean droplet size and uniform low dispersion. Mean droplet size was also reduced below 400 nanometers by means of passing hot composition through high pressure homogenizer.

Example 9

Ketoconazole or Itraconazole Composition

| INGREDIENT | % w/w |
|---|---|
| Ketoconazole | 5.0 |
| Caprylic/Capric triglyceride | 10.0 |
| Glyceryl monostarate | 2.0 |
| Sucrose ester | 2.0 |
| Glycerin | To 100 |

Vegetable hard capsules regular 00 size, were filled with Ketoconazole composition of example 8 and have been found stable and retained shape and appearance following 30 days storage in plastic bag at 40° C. and 75 relative humidity.

Example 10

Ketoconazole or Itraconazole Composition

| INGREDIENT | % w/w |
|---|---|
| Ketoconazole | 5.0 |
| Caprylic/Capric triglyceride | 10.0 |
| Stearic acid | 2.0 |
| Glyceryl monostarate | 2.0 |
| Polyglyceryl-10 stearate | 2.0 |
| Sorbitan oleate | 1.0 |
| Ethyl cellulose | 1.0 |
| Macrogol 4000 | 30.0 |
| Propylene glycol | To 100 |

Example 11

Ketoconazole or Itraconazole Composition

| INGREDIENT | % w/w |
|---|---|
| Ketoconazole | 4.0 |
| Triacetin | 6.0 |
| Hydrogenated palm oil | 6.0 |
| Sucrose ester | 2.0 |
| Glycerin | To 100 |

Example 12

Tacrolimus or Picrolimus Composition

| INGREDIENT | % w/w |
|---|---|
| Tacrolimus | 4.0 |
| Hydrogenated castor oil | 6.0 |
| Triacetin | 4.0 |

-continued

| INGREDIENT | % w/w |
| --- | --- |
| Sucrose ester | 2.0 |
| Propylene glycol | 22.0 |
| Chitosan | 1.0 |
| Macrogol 4000 | To 100 |

Example 13

Hydrocortisone Composition

| INGREDIENT | % w/w |
| --- | --- |
| Hydrocortisone | 2.0 |
| Caprylic/Capric triglyceride | 8.0 |
| Triacetin | 2.0 |
| Sucrose ester | 4.0 |
| Glycerin | 83 |

Example 14

Genistein Composition

| INGREDIENT | % w/w |
| --- | --- |
| Genistein | 1.0 |
| Caprylic/Capric triglyceride | 12.0 |
| Glyceryl monostearate | 2.0 |
| Sucrose ester | 4.0 |
| Glycerin | To 100 |

Example 15

Cyclosporin Composition

| INGREDIENT | % w/w |
| --- | --- |
| Cyclosporin | 4.0 |
| Caprylic/Capric triglyceride | 8.0 |
| Triacetin | 4.0 |
| Oleic acid | 2.0 |
| Polyglyceryl-10 oleate | 2.0 |
| Sucrose ester | 2.0 |
| Glycerin | To 100 |

Cyclosporin is co-melted with the Caprylic/Capric triglyceride, Triacetin, Oleic acid, Polyglyceryl-10 oleate, and Sucrose ester until homogeneous. Hot glycerin is slowly added while mixing and composition is homogenized. Mean droplet size is 600 nanometers and Cyclosporin is uniformly dispersed in the composition while majority of Cyclosporin is non-crystalline.

Example 16

Cold Process, Principle Base Composition

| INGREDIENT | % w/w |
| --- | --- |
| A drug | 2.0-10.0 |
| Caprylic/Capric triglyceride | 10.0 |
| Pemulene TR2 | 1.0 |
| Polyethylene glycol 400 | 40.0 |
| Glycerin | To 100 |

The preparation of this example composition is made at ambient temperature or optionally mild heating and is preferably suitable for formulation of heat sensitive bioactive agents, drugs. This composition will also tolerate many co-solvents such as triacetin or dimethyl isosorbide.

Example 17

Cyclosporin or Peptide Drug Cold Process Composition

| INGREDIENT | % w/w |
| --- | --- |
| Cyclosporin | 2.0 |
| Caprylic/Capric triglyceride | 8.0 |
| Triacetin | 4.0 |
| Pemulene TR2 | 1.0 |
| Macrogol 400 | 40.0 |
| Glycerin | To 100 |

Tri-ethanol-amine or Sodium hydroxide is added to adjust the pH of the composition to suite peptide required pH for optimal stability.

Example 18

Amphotericin Composition

| INGREDIENT | % w/w |
| --- | --- |
| Amphotericin A or B | 2.0 |
| Caprylic/Capric triglyceride | 6.0 |
| Dimethyl isosorbide | 2.0 |
| Lecithin | 2.0 |
| Sucrose ester | 2.0 |
| Glyceryl monostearate | 0.5 |
| Glycerin | To 100 |

Example 19

Ceftriaxone Composition

| INGREDIENT | % w/w |
| --- | --- |
| Ceftriaxone | 20.0 |
| Caprylic/Capric triglyceride | 5.0 |
| Oleic acid | 5.0 |
| Glyceryl monostearate | 2.0 |
| Sucrose ester | 2.0 |
| Stearic acid | 5.0 |
| Glycerin | To 100 |

Example 20

Griseofulvin Composition

| INGREDIENT | % w/w |
| --- | --- |
| Griseofulvin | 10.0 |
| Liquid paraffin | 10.0 |
| Lanolin fatty acid ester | 5.0 |
| Hydroxypropylcellulose | 4.0 |
| Dimethyl isosorbide | To 100 |

Example 21

COX-2 Inhibitor Composition

| INGREDIENT | % w/w |
| --- | --- |
| COX-2 inhibitor | 10.0 |
| Paraffin wax | 10.0 |
| Lanolin fatty acid ester | 5.0 |
| Hydroxypropylcellulose | 4.0 |
| Glycerin | 40.0 |
| Dimethyl isosorbide | To 100 |

Example 22

Progesteron or Estradiol Composition

| INGREDIENT | % w/w |
| --- | --- |
| Progesterone | 1.0 |
| Paraffin wax | 10.0 |
| Lanolin fatty acid ester | 5.0 |
| Hydroxypropylcellulose | 4.0 |
| Glycerin | 40.0 |
| Dimethyl isosorbide | To 100 |

Example 23

Omega 3 Fatty Acids Composition

| INGREDIENT | % w/w |
| --- | --- |
| EPA + DMA (70% omega-3 Fish oil) | 20.0 |
| Tocopherol succinate | 2.0 |
| Sucrose ester | 4.0 |
| Hydroxypropylcellulose | 2.0 |
| Ethylene Diamine Tetra Acetic Acid | 0.4 |
| Glycerin | To 100 |

Example 24

Glibenclamide Composition

| INGREDIENT | % w/w |
| --- | --- |
| Glibenclamide | 2.0 |
| Coconut oil | 12.0 |
| Sucrose ester | 2.0 |
| Tocopheryl linoleate | 2.0 |
| Glycerin | To 100 |

Example 25

Etoposide or Taxol Composition

| INGREDIENT | % w/w |
| --- | --- |
| Etoposide | 10.0 |
| Triacetin | 4.0 |
| Tocopheryl linoleate | 4.0 |
| Glyceryl monosteararte | 2.0 |
| Dimethyl isosorbide | 2.0 |
| Pemulene TR2 | 1.0 |
| Sucrose ester | 2.0 |
| Glycerin | To 100 |

Etoposide is co-melted on oil bath with Triacetin, Tocopheryl linoleate, Glyceryl monosteararte, Dimethyl isosorbide, and sucrose ester until homogeneouse liquid is obtained and majority of Etoposide crystals melt as observed with light microscope. Hot glycerin is slowly added under vigorous mixing. Pemulene is sprinkled into the composition under mixing. Composition is homogenized and cooled to room temperature. Composition is filled in capsules. Mean droplet size is controlled between 2,000-200 nanometers by magnitude of homogenization and equipment selection. Droplet size is preserved upon dilution and mixing with simulated intestinal fluids.

Example 26

Acyclovir or Nucleoside Analogue Composition

| INGREDIENT | % w/w |
|---|---|
| Acyclovir | 10.0 |
| MCT oil | 5.0 |
| Sucrose ester | 5.0 |
| Hydroxypropylcellulose | 4.0 |
| Glycerin | 40.0 |
| Dimethyl isosorbide | To 100 |

Acyclovir is dissolved in Dimethyl isosorbide at 50° C. and MCT oil and Sucrose esters are added and co-melted at 70° C. Hydroxypropylcellulose is added to the glycerin and heated to 90° C. and added slowly to the Acyclovir phase with homogenization. Homogenization continues until cooling to room temperature.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A pharmaceutical or nutritional composition, in the form of a stable non-hydrous emulsion dispersion, comprising:
   a) an originally crystalline hydrophobic bioactive agent,
   b) an oily solvent;
   c) a non-hydrous hydrophilic solvent; and
   d) an emulsifying stabilizer present in an amount of 0.1 to 10% of the emulsion dispersion,
   wherein said bioactive agent is dissolved or dispersed in said oily solvent such that the majority of the bioactive agent is non-crystalline and does not re-crystallize or only slightly crystallizes upon storage, wherein said oily solvent comprises the internal phase of the emulsion dispersion, and wherein said non-hydrous hydrophilic solvent comprises the continuous phase of said emulsion dispersion,
   whereby sub-micron mean droplet size is obtained upon dilution of the composition with physiological fluids.

2. The pharmaceutical or nutritional composition of claim 1, wherein facilitated dissolution of the bioactive agent is obtained.

3. The pharmaceutical or nutritional composition of claim 1, wherein facilitated solubilizing effect of the bioactive agent in physiological fluids is obtained and oily particles retain their size upon dilution with physiological fluids for the time needed for systemic absorption.

4. The pharmaceutical or nutritional composition of claim 1, wherein at least a major portion of the bioactive agent is uniformly and molecularly dispersed in the composition.

5. The pharmaceutical or nutritional composition of claim 1, wherein said bioactive agent is present in an amount ranging from about 0.1 to about 40% wt/wt.

6. The pharmaceutical or nutritional composition of claim 1, wherein said oily solvent is present in an amount ranging from about 1 to about 40% wt/wt.

7. The pharmaceutical or nutritional composition of claim 1, wherein said emulsifying stabilizer is present in an amount ranging from about 0.1 to about 5% wt/wt.

8. The pharmaceutical or nutritional composition of claim 1, wherein the emulsifying stabilizer is selected from the group consisting of: (i) non-ionic condensation products of a carbohydrate and a fatty acid, wherein the carbohydrate is sucrose, glucoside or sorbitan; (ii) mono- or di-glycerides of fatty acids; (iii) sucroglycerides; (iv) polyglycerol esters of fatty acids; (v) propane-1,2-diol esters of fatty acids; and (vi) poly acid carbohydrate esters of fatty acids.

9. The pharmaceutical or nutritional composition of claim 1, wherein said low solubility bioactive agent is selected from the group consisting of a drug, a peptide or polypeptide, a nucleotide and a glycolipid and has an aqueous solubility of less than 10 mg/ml.

10. The pharmaceutical or nutritional composition of claim 1, wherein the non-hydrous and hydrophilic phase comprises a polyalcohol selected from the group consisting of glycerin, propylene glycol, polyethylene glycol, dimethyl isosorbide, and mixtures thereof.

11. The pharmaceutical or nutritional composition of claim 1, wherein the composition is liquid at temperatures ranging from 50° C. to 100° C. and semi-solid at ambient temperature.

12. A process for producing the pharmaceutical or nutritional composition according to claim 1 in the form of a semi-solid emulsion, the process comprising:
   A) heating and co-melting the bioactive agent, the oily solvent and the emulsifying stabilizer until a clear solution devoid of solid material is obtained;
   B) heating the non-hydrous hydrophilic solvent to 80° C.-100° C.;
   C) adding the hot non-hydrous solvent of (B) to the hot oily phase of (A) in increments under stirring and mixing, thus obtaining an emulsion; and
   D) homogenizing the emulsion (C) until the hot liquid cools, thus obtaining the desired semi-solid emulsion.

13. A method for administering an originally crystalline hydrophobic bioactive agent with facilitated dissolution and oral availability of the bioactive agent, comprising orally administering to a patient in need a pharmaceutical or nutritional composition in accordance with claim 1.

14. The pharmaceutical composition of claim 1, wherein the bioactive agent is a drug.

15. The pharmaceutical composition of claim 1, wherein at least 60% of the drug is in amorphous form.

16. The pharmaceutical composition of claim 15, wherein at least 80% of the drug is in amorphous form.

17. The pharmaceutical composition of claim 16, wherein at least 90% of the drug is in amorphous form.

18. The pharmaceutical or nutritional composition of claim 9 having an aqueous solubility of less than 1 mg/mL.

19. The pharmaceutical or nutritional composition of claim 18 having an aqueous solubility of less than 0.1 mg/mL.

20. The pharmaceutical or nutritional composition of claim 1, wherein the bioactive agent is selected from the group consisting of vitamins, chemotherapeutics, antimycotics, oral contraceptives, nicotine or nicotine replacement agents, minerals, analgesics, antacids, muscle relaxants, antihistamines, decongestants, anesthetics, antitussives, diuretics, anti-inflammatories, antibiotics, antivirals, anti-amoebics, anti-allergics, anti-emetics, psychotherapeutic agents, anti-diabetic agents, cardiovascular agents, antimicrobial agents, antifungal agents, anxiolytics, sedatives, hypnotics, migraine relieving agents, immune modulators, rejuvenation agents, astringents, coronary drugs, cholesterol and triglyceride lowering drugs, drugs against motion sickness, nutraceuticals and nutritional supplements.

* * * * *